US009069345B2

(12) United States Patent
McCready et al.

(10) Patent No.: US 9,069,345 B2
(45) Date of Patent: Jun. 30, 2015

(54) CONTROLLING A MANUFACTURING PROCESS WITH A MULTIVARIATE MODEL

(75) Inventors: Christopher Peter McCready, London (CA); Svante Bjarne Wold, Hollis, NH (US)

(73) Assignee: MKS Instruments, Inc., Andover, MA (US)

( * ) Notice: Subject to any disclaimer, the term of this patent is extended or adjusted under 35 U.S.C. 154(b) by 647 days.

(21) Appl. No.: 12/358,864

(22) Filed: Jan. 23, 2009

(65) Prior Publication Data

US 2010/0191361 A1    Jul. 29, 2010

(51) Int. Cl.
| G06F 19/00 | (2011.01) |
| G06F 7/60 | (2006.01) |
| G06F 17/10 | (2006.01) |
| G05B 13/04 | (2006.01) |

(52) U.S. Cl.
CPC .... *G05B 13/048* (2013.01); *G05B 2219/42061* (2013.01)

(58) Field of Classification Search
CPC ................. G05B 13/048; G05B 2219/42061; G05B 15/02; G05B 17/02; G05B 23/0221
USPC ............................... 700/103–105, 108; 703/2
See application file for complete search history.

(56) References Cited

U.S. PATENT DOCUMENTS

| 5,135,688 A | 8/1992 | Nakamura et al. |
| 5,149,472 A | 9/1992 | Suganuma |
| 5,173,224 A | 12/1992 | Nakamura et al. |
| 5,347,446 A | 9/1994 | Iino et al. |
| 5,403,433 A | 4/1995 | Morrison et al. ............. 156/626 |
| 5,408,405 A | 4/1995 | Mozumder et al. ........... 364/151 |
| 5,442,562 A | 8/1995 | Hopkins et al. ............... 364/468 |
| 5,469,361 A | 11/1995 | Moyne .......................... 364/468 |
| 5,479,340 A * | 12/1995 | Fox et al. ........................ 700/33 |
| 5,485,471 A | 1/1996 | Bershteyn |
| 5,544,256 A | 8/1996 | Brecher et al. ................ 382/149 |
| 5,710,700 A | 1/1998 | Kurtzberg et al. ............ 364/149 |
| 5,786,999 A | 7/1998 | Spahr et al. |
| 5,815,397 A | 9/1998 | Saito et al. |

(Continued)

FOREIGN PATENT DOCUMENTS

| DE | 101 14 211 A1 | 11/2001 |
| DE | 100 40 731 A1 | 3/2002 |

(Continued)

OTHER PUBLICATIONS

U.S. Appl. No. 12/044,346, filed Mar. 7, 2008, Hendler et al.

(Continued)

*Primary Examiner* — Kenneth M Lo
*Assistant Examiner* — Jason Lin
(74) *Attorney, Agent, or Firm* — Proskauer Rose LLP

(57) ABSTRACT

A method, controller, and system for controlling a manufacturing process (batch-type or continuous-type) with a multivariate model are described. Dependent variable data and manipulated variable data are received. Dependent variable data represents values of uncontrolled process parameters from a plurality of sensors. Manipulated variable data represents controlled or setpoint values of controllable process parameters of a plurality of process tools. A predicted operational value, multivariate statistic, or both are determined based on the received data, and operating parameters of the manufacturing process are determined based on the predicted score, multivariate statistic, or both.

30 Claims, 7 Drawing Sheets

(56) References Cited

U.S. PATENT DOCUMENTS

| | | | |
|---|---|---|---|
| 5,885,624 A | 3/1999 | Katsuta et al. | |
| 5,900,633 A | 5/1999 | Solomon et al. | |
| 5,949,678 A | 9/1999 | Wold et al. | 364/188 |
| 5,993,704 A | 11/1999 | Bader | |
| 5,997,778 A | 12/1999 | Bulgrin | |
| 6,090,318 A | 7/2000 | Bader et al. | |
| 6,153,115 A | 11/2000 | Le et al. | 216/60 |
| 6,336,082 B1 | 1/2002 | Nguyen et al. | 702/179 |
| 6,354,145 B1 | 3/2002 | Fransson et al. | 73/61.52 |
| 6,368,883 B1 | 4/2002 | Bode et al. | 438/14 |
| 6,442,445 B1 | 8/2002 | Bunkofske et al. | 700/108 |
| 6,453,246 B1 | 9/2002 | Agrafiotis et al. | 702/27 |
| 6,456,899 B1 | 9/2002 | Gleason et al. | 700/212 |
| 6,528,331 B1 | 3/2003 | Bode et al. | 438/14 |
| 6,556,884 B1 | 4/2003 | Miller et al. | 700/121 |
| 6,564,119 B1 | 5/2003 | Vaculik et al. | 700/146 |
| 6,584,368 B2 | 6/2003 | Bunkofske et al. | 700/83 |
| 6,594,620 B1 | 7/2003 | Qin et al. | 702/185 |
| 6,607,577 B2 | 8/2003 | Vaculik et al. | 75/375 |
| 6,678,569 B2 | 1/2004 | Bunkofske et al. | 700/108 |
| 6,682,669 B2 | 1/2004 | Bulgrin et al. | |
| 6,718,224 B2 | 4/2004 | Firth et al. | 700/121 |
| 6,721,616 B1 | 4/2004 | Ryskoski | 700/108 |
| 6,741,903 B1 | 5/2004 | Bode et al. | 700/121 |
| 6,801,831 B2 | 10/2004 | Sasaki | |
| 6,830,939 B2 | 12/2004 | Harvey et al. | 438/8 |
| 6,839,655 B2 | 1/2005 | Gross et al. | 702/179 |
| 6,876,931 B2 | 4/2005 | Lorenz et al. | 702/22 |
| 6,917,839 B2 | 7/2005 | Bickford | 700/30 |
| 6,967,899 B1 | 11/2005 | O'Brien, Jr. et al. | 367/131 |
| 6,968,253 B2 | 11/2005 | Mack et al. | 700/121 |
| 6,975,944 B1 | 12/2005 | Zenhausern | 702/22 |
| 6,983,176 B2 | 1/2006 | Gardner et al. | 600/310 |
| 7,003,490 B1 | 2/2006 | Keyes | 705/38 |
| 7,031,800 B2 | 4/2006 | Bulgrin | |
| 7,043,401 B2 | 5/2006 | Taguchi et al. | 702/183 |
| 7,062,417 B2 | 6/2006 | Kruger et al. | 703/2 |
| 7,072,794 B2 | 7/2006 | Wittkowski | 702/179 |
| 7,107,491 B2 | 9/2006 | Graichen et al. | 714/37 |
| 7,151,976 B2 | 12/2006 | Lin | 700/108 |
| 7,189,964 B2 | 3/2007 | Castro-Perez et al. | |
| 7,191,106 B2 | 3/2007 | Minor et al. | 703/2 |
| 7,198,964 B1 | 4/2007 | Cherry et al. | |
| 7,216,005 B2 | 5/2007 | Shioiri et al. | |
| 7,313,454 B2 | 12/2007 | Hendler et al. | 700/110 |
| 7,328,126 B2 | 2/2008 | Chamness | |
| 7,433,743 B2* | 10/2008 | Pistikopoulos et al. | 700/52 |
| 7,465,417 B2 | 12/2008 | Hutson et al. | |
| 7,597,827 B2 | 10/2009 | Frey | |
| 7,622,308 B2 | 11/2009 | Hendler et al. | |
| 8,135,481 B2* | 3/2012 | Blevins et al. | 700/51 |
| 8,271,103 B2* | 9/2012 | Hendler et al. | 700/31 |
| 8,360,040 B2* | 1/2013 | Stewart et al. | 123/672 |
| 2002/0019672 A1* | 2/2002 | Paunonen | 700/17 |
| 2002/0038926 A1 | 4/2002 | Vaculik et al. | 266/90 |
| 2002/0107858 A1* | 8/2002 | Lundahl et al. | 707/100 |
| 2002/0143472 A1 | 10/2002 | Mutter | 702/20 |
| 2003/0011376 A1 | 1/2003 | Matsushita et al. | 324/500 |
| 2003/0065462 A1 | 4/2003 | Potyrailo | 702/81 |
| 2003/0182281 A1 | 9/2003 | Wittkowski | 707/5 |
| 2004/0055888 A1 | 3/2004 | Wikiel et al. | 205/81 |
| 2004/0064259 A1 | 4/2004 | Haaland et al. | |
| 2004/0064357 A1 | 4/2004 | Hunter et al. | 705/10 |
| 2004/0083065 A1 | 4/2004 | Daniel et al. | |
| 2004/0116814 A1 | 6/2004 | Stranc et al. | 600/473 |
| 2004/0122859 A1 | 6/2004 | Gavra et al. | 707/104.1 |
| 2004/0153815 A1 | 8/2004 | Volponi | 714/37 |
| 2004/0186603 A1 | 9/2004 | Sanford et al. | 700/95 |
| 2004/0215424 A1 | 10/2004 | Taguchi et al. | 702/189 |
| 2004/0225377 A1 | 11/2004 | Kokotov et al. | 700/1 |
| 2004/0228186 A1 | 11/2004 | Kadota | 365/202 |
| 2004/0254762 A1 | 12/2004 | Hopkins et al. | |
| 2004/0259276 A1* | 12/2004 | Yue et al. | 438/5 |
| 2005/0010318 A1* | 1/2005 | Lev-Ami et al. | 700/109 |
| 2005/0028932 A1 | 2/2005 | Shekel et al. | 156/345.15 |
| 2005/0037515 A1 | 2/2005 | Nicholson et al. | 436/173 |
| 2005/0043902 A1 | 2/2005 | Haaland et al. | 702/30 |
| 2005/0045821 A1 | 3/2005 | Noji et al. | 250/311 |
| 2005/0060103 A1 | 3/2005 | Chamness | 702/30 |
| 2005/0130321 A1 | 6/2005 | Nicholson et al. | 436/518 |
| 2005/0251276 A1 | 11/2005 | Shen | 700/108 |
| 2005/0268197 A1* | 12/2005 | Wold | 714/746 |
| 2006/0012064 A1* | 1/2006 | Hutson et al. | 264/40.1 |
| 2006/0039598 A1 | 2/2006 | Kim et al. | 382/145 |
| 2006/0058898 A1 | 3/2006 | Emigholz et al. | 700/29 |
| 2006/0111804 A1 | 5/2006 | Lin | 700/110 |
| 2006/0122807 A1 | 6/2006 | Wittkowski | 702/179 |
| 2006/0149407 A1* | 7/2006 | Markham et al. | 700/108 |
| 2006/0155410 A1* | 7/2006 | Yamartino | 700/108 |
| 2006/0184264 A1 | 8/2006 | Willis et al. | 700/108 |
| 2006/0259163 A1 | 11/2006 | Hsiung et al. | |
| 2007/0021859 A1 | 1/2007 | Lev-Ami et al. | 700/121 |
| 2008/0010531 A1 | 1/2008 | Hendler et al. | 714/33 |
| 2008/0015814 A1 | 1/2008 | Harvey, Jr. et al. | |
| 2008/0082181 A1 | 4/2008 | Miller et al. | |
| 2008/0104003 A1 | 5/2008 | Macharia et al. | |
| 2008/0221720 A1 | 9/2008 | Hendler et al. | 700/109 |
| 2008/0275587 A1 | 11/2008 | Adams | |
| 2009/0037013 A1 | 2/2009 | Hendler et al. | 700/103 |
| 2009/0055140 A1 | 2/2009 | Kettaneh et al. | 703/2 |
| 2009/0164171 A1 | 6/2009 | Wold et al. | |
| 2009/0287320 A1* | 11/2009 | MacGregor et al. | 700/29 |
| 2010/0057237 A1 | 3/2010 | Kettaneh et al. | |
| 2010/0082120 A1* | 4/2010 | Stephenson et al. | 700/29 |
| 2010/0191361 A1 | 7/2010 | McCready et al. | |

FOREIGN PATENT DOCUMENTS

| | | |
|---|---|---|
| EP | 0 524 317 A1 | 1/1993 |
| GB | 2 394 312 A | 4/2004 |
| GB | 2 441 640 A | 3/2008 |
| JP | 02-120019 | 5/1990 |
| JP | H04-266101 | 2/1991 |
| WO | 03/085504 | 10/2003 |
| WO | 03/103024 | 12/2003 |
| WO | 2004/019147 | 3/2004 |
| WO | 2004/046835 | 6/2004 |
| WO | 2007/046945 A2 | 4/2007 |
| WO | 2009/151419 | 12/2009 |

OTHER PUBLICATIONS

Chen et al., "Plasma etch modeling using optical emission spectroscopy," J. Vac. Sci. Technol. A 14(3), May/Jun. 1996, pp. 1901-1906.
Eriksson et al., *Multi- and Megavariate Data Analysis: Part I Basic Principles and Applications* (2nd. ed.), Umetrics Academy (2006).
Eriksson et al., *Multi- and Megavariate Data Analysis: Part II Advanced Applications and Method Extensions* (2nd. ed.), Umetrics Academy (2006).
Gallagher et al., "Development and Benchmarking of Multivariate Statistical Process Control Tools for a Semiconductor Etch Process: Improving Robustness through Model Updating," IFAC ADCHEM'97, 78-83, Banff, Canada, Jun. 1997.
Goodlin et al., "Simultaneous Fault Detection and Classification for Semiconductor Manufacturing Tools," 201st Meeting of the Electrochemical Society, International Symposium on Plasma Processing XIV, Abs. 413, Philadelphia, PA, May 2002, 16 pages.
Goodlin et al., "Simultaneous Fault Detection and Classification for Semiconductor Manufacturing Tools," Journal of the Electrochemical Society, 150 (12), May. 12, 2002, pp. G778-G784.
"Hotelling's T squared," Engineering Statistics Handbook [online], Ch. 6.5.4.3, 2 pages [retrieved on Jan. 13, 2006]. Retrieved from the Internet: <URL: http://www.itl.nist.gov/div898/handbook/pmc/section5/pmc543.htm>.
Kresta et al., "Multivariate Statistical Monitoring of Process Operating Performance," The Canadian Journal of Chemical Engineering, vol. 69, Feb. 1991, pp. 35-47.
Jiang et al., "Fault Diagnosis for Batch Processes Based on Improved MFDA," 2005 IEEE International Conference on Systems Man, and Cybernetics, vol. 4, pp. 3420-3425, Oct. 10-12, 2005, IEEE, Piscataway, NJ, (ISBN 0-7803-9298-1).

(56) References Cited

OTHER PUBLICATIONS

Lymberopoulos et al., "Advanced Process Control Comes of Age," Semiconductor International [online], 5 pages, Jul. 1, 2004 [retrieved on Nov. 19, 2008]. Retrieved from the Internet: <URL: http://www.semiconductor.net/index.asp?layout=articlePrint&articleID=CA430898>.

Martin et al., "Multivariate Statistical Process Control and Process Performance Monitoring," IFAC Dynamics and Control of Process Systems, 1999, XP-000911903, pp. 347-356.

Mason et al., "Applying Hotelling's $T^2$ Statistic to Batch Processes," J. Quality Technology, vol. 33, No. 4, Oct. 2001, pp. 466-479.

"Pearson's Correlation Coefficient," Teach/Me Data Analysis [online], 2 pages [retrieved on Dec. 9, 2005]. Retrieved from the Internet: <URL: http://www.vias.org/tmdataanaleng/cc_corr_coeff.html>.

"Process leaps without new hardware," EuroAsia Semiconductor [online], Nov. 2004, 3 pages [retrieved on Nov. 19, 2008]. Retrieved from the Internet: <URL http://www.euroasiasemiconductor.com/print_version.php?id=5677>.

Skumanich et al., "Advanced etch applications using tool-level data," <URL: http://sst.pennnet.com/articles/article_display.cfm?section=archi&article_id=206470&vers . . . >.

Smith et al., "From Sensor Data to Process Control: A Networked Framework," Semiconductor Manufacturing Magazine, Jul. 2004, 6 pages.

Smith et al., "Practical, Real-Time Multivariate FDC," Semiconductor International [online], Dec. 1, 2004, 6 pages [retrieved on Dec. 16, 2005]. Retrieved from the Internet: <URL: http://www.reed-electronics.com/semiconductor/index.asp?layout=articlePrint&articleID=CA483628>.

Solomon et al., "Real-Time Measurement of Film Thickness, Composition, and Temperature by FT-IR Emission and Reflection Spectroscopy," in *Semiconductor Characterization: Present Status and Future Needs*, (Bullis et al.) AIP Press, 1996, pp. 544-548.

"TOOLweb Blue Box Professional: Enabling High Speed, Multi-User Connectivity and Data Sharing," Control & Information Technology [online], Mar. 2005, 4 pages [retrieved on Nov. 19, 2008]. Retrieved from the Internet: <URL: http://www.mksinst.com/docs/ur/ipcblueds.pdf>.

"TOOLweb Applications Support: AEC/APC Applications Engineering, Integration and Deployment Support," Control & Information Technology [online], Sep. 2005, 4 pages [retrieved on Nov. 19, 2008]. Retrieved from the Internet: <URL: http://www.mksinst.com/docs/UR/TWT3DS.pdf>.

"TOOLweb: APC & e-Diagnostics Suite," Control & Information Technology [online], 4 pages [retrieved on Nov. 19, 2008]. Retrieved from the Internet: <URL: http://www.mksinst.com/docs/ur/twmvads.pdf>.

"TOOLweb SenseLink: Web-Enables Existing Sensors," Control & Information Technology [online], 4 pages [retrieved on Nov. 19, 2008]. Retrieved from the Internet: <URL: http://www.mksinst.com/docs/ur/twsenselinkds.pdf>.

"User's Guide to SIMCA-P, SIMCA-P+," Umetrics AB, Version 11.0, May 17, 2005, pp. 1-456.

Wang et al., "Process Monitoring in Principal Component Subspace: Part 1. Fault Reconstruction Study," 2004 IEEE International Conference on Systems, Man and Cybernetics, The Hague, The Netherlands, vol. 6, Oct. 10-13, 2004, pp. 5119-5124.

Wold et al., "Hierarchical Multiblock PLS and PC Models for Easier Model Interpretation and as an Alternative to Variable Selection," Journal of Chemometrics, vol. 10, 1996, pp. 463-482.

Wold et al., "Modelling and diagnostics of batch processes and analogous kinetic experiments," Chemometrics and Intelligent Laboratory Systems, vol. 44, Nos. 1-2, 1998, pp. 331-340.

Wold et al., "2.10 Batch Process Modeling and MSPC," in *Comprehensive Chemometrics: Chemical and Biochemical Data Analysis*, (Brown et al. Eds.), Oxford, UK; Elsevier, 37 pages (2009).

Xu et al., "A Novel Combination Method for On-Line Process Monitoring and Fault Diagnosis," IEEE ISIE 2005, Dubrovnik, Croatia, Jun. 20-23, 2005, pp. 1715-1719.

Fugee Tsung, Jianjun Shi, C.F. J. Wu: "Joint Monitoring of PID-Controlled Processes" Journal of Quality Technology, vol. 31, No. 3, Jul. 1, 1999, pp. 275-285, XP002579609.

Ahmed S. F., "A New Approach in Industrial Automation Application "Embedded System Design for Injection Molding Machine, IEEE Xplore, Oct. 29, 2009, 5 pages.

Bai, et al., "IMPOS: A Method and System for Injection Molding Optimization," IEEE Xplore, Oct. 29, 2009, 5 pages.

C. E. Castro, et al., "Multiple criteria optimization with variability considerations in injection molding," *Polymer Engineering and Science*, vol. 47, p. 400, 2007.

C. M. Seaman, et al., "Multiobjective optimization of a plastic injection molding process," *IEEE Transactions on Control Systems Technology*, vol. 2, No. 3, pp. 157-168, 1994.

Chen, et al., "Application of Advanced Process Control in Plastic Injection Molding," IEEE Xplore, Oct. 29, 2009, 6 pages.

Chen, et al., "Injection Molding Quality Control by Integrating Weight Feedback into a Cascade Closed-Loop Control System," Polymer Engineering and Science, 2007, 11 pages.

International Search Report for International Application No. PCT/US2010/021486, Date of Mailing Jul. 5, 2010 (20 pages total).

D. Kazmer and C. Roser, "Evaluation of Product and Process Design Robustness," *Research in Engineering Design*, vol. 11, pp. 20-30, 1999.

D. Kazmer and S. Westerdale, "A model-based methodology for on-line quality control," *Int J Adv Manuf Technol*, vol. 42, pp. 280-292, 2009.

D. Kazmer, "Chapter 13: Quality Control," in *Plastics Manufacturing Systems Engineering*, ed Munich: Carl Hanser Verlag, 2009, pp. 387-418.

D. O. Kazmer, et al., "A Comparison of Statistical Process Control (SPC) and On-Line Multivariate Analyses (MVA) for Injection Molding," *International Polymer Processing*, vol. 23, pp. 447-458, 2008.

Dubay, et al., "An Investigation on the Application of Predictive Control for Controlling Screw Position and Velocity on an Injection Molding Machine," Polymer Engineering and Science, 2007, 10 pages.

Fung, et al., "Application of a Capacitive Transducer for Online Part Weight Prediction and Fault Detection in Injection Molding," Polymer Engineering and Science, 2007, 7 pages.

G. Sherbelis, et al., "The Methods and benefits of Establishing a Process Window," in *Proceedings of the 55th Annual Technical Conference, ANTEC*, Part 1 (of 3), 1997, pp. 545-550.

J. W. Mann, "Process Parameter Control: the Key to Optimization," Plastics Engineering, vol. 30, pp. 25-27, 1974.

Knights, M., "Injection Mold Balance Unbalanced," Plastics Technology, http://www.ptonline.com/articles/200811fal.html; Nov. 2008, 5 pages.

Li, et al., "A Real-Time Process Optimization System for Injection Molding," Polymer Engineering and Science, 2009, 10 pages.

Li, et al., "Predicting the Parts Weight in Plastic Injection Molding Using Least Squares Support Vector Regression," IEEE Transactions on Systems, Man, and Cybernetics—Part C: Applications and Reviews, vol. 38, No. 6, Nov. 2008, 7 pages.

Liu, et al, "Identification and Autotuning of Temperature-Control System With Application to Injection Molding," IEEE Transactions on Control Systems Technology, vol. 17, No. 6, Nov. 2009, 13 pages.

M. Berins, "Standards for Molding Tolerances," in *SPI Plastics Engineering Handbook of the Society of the Plastics Industy, Inc.* (5th Edition) 5th ed: Kluwer Academic Publishers, 1991, pp. 821-844.

Mei, et al., "The Optimization of Plastic Injection Molding Process Based on Support Vector Machine and Genetic Algorithm," International Conference on Intelligent Computation Technology and Automation, 2008, 4 pages.

N. M. Morris and W. B. Rouse, "The Effects of Type of Knowledge Upon Human Problem Solving in a Process Control Task," *IEEE Transactions on Systems, Man and Cybernetics*, vol. SMC-15, No. 6 pp. 698-707, 1985.

N. Yonehara and I. Ito, "Finding an optimal operation conditions of plastic molding by artificial neural network," *Nippon Kikai Gakkai Ronbunshu, C Hen/Transactions of the Japan Society of Mechanical Engineers, Part C*, vol. 63, pp. 3538-3543, 1997.

(56) References Cited

OTHER PUBLICATIONS

P. Knepper and D. Kazmer, "Multi-objective velocity profile optimization," Charlotte, NC, United States, 2006, pp. 1093-1097.

R. H. Myers and D. C. Montgomery, "Response Surface Methodology: Process and Product Optimization Using Designed Experiments," in *Wiley Series in Probability and Statistics*, ed: Wiley Interscience, 1995, p. 248.

R. Ivester, et al., "Automatic tuning of injection molding by the virtual search method," *Journal of Injection Molding*, vol. 2/No. 3, Sep. 1998.

Shu, et al., "PID Neural Network Temperature Control System in Plastic Injecting-moulding Machine," Third International Conference on Natural Computation, 2007, 5 pages.

State space (controls), State space (controls)—Wikipedia, the free encyclopedia [online], 11 pages [retrieved on Sep. 14, 2010]. Retrieved from the Internet: <URL: http://en.wikipedia.org/wiki/State_Space_(controls)>.

Tan et al., "Adaptive Control of Ram Velocity for the Injection Moulding Machine," IEEE Transactions on Control Systems Technology, vol. 9, No. 4, Jul. 2001, 9 pages.

Triefenbach, F., "Design of Experiments: The D-Optimal Approach and Its Implementation as a Computer Algorithm," Bachelor's Thesis in Information and Communication Technology, Jan. 15, 2008, 84 pages.

Yang J. H., "Nonlinear Adaptive Control for Injection Molding Machines," IEEE Xplore, Oct. 29, 2009, 6 pages.

You et al., "Research on Temperature Measure and Control Method in Mold-Temperature-Control Solidification," IEEE International Conference on Control and Automation WeCP-18, Guangzhou, China—May 30 to Jun. 1, 2007, 4 pages.

The Singapore Written Opinion and Search Report for Application No. 201105312-1, mailed on Sep. 14, 2012 (20 pgs.).

* cited by examiner

CONTROLLING A MANUFACTURING PROCESS WITH A MULTIVARIATE MODEL

TECHNICAL FIELD

The invention generally relates to data analysis and control of a manufacturing process, and particularly to controlling a manufacturing process with a multivariate model.

BACKGROUND

In many industries, very large data sets are collected both in manufacturing, and in the research and development. Manufacturing processes are sometimes categorized as "batch" manufacturing processes or "continuous" manufacturing processes. In batch manufacturing processes, a series of steps with a beginning step and an ending step are performed on a set of raw and/or processed materials to produce an output. In some batch processes, processing occurs at a single workstation (e.g., a chamber or container) involving one or more process tools (e.g., process tools within the chamber or container). Examples of batch manufacturing processes include semiconductor wafer processing (e.g., processing a single wafer results in a set of chips), pharmaceutical processing (e.g., the process results in an intermediate or final output set of chemicals or drugs), or biotechnology processing (e.g., the process results in a particular biological fermentation or cell culture process). In continuous manufacturing processes, materials are manufactured, processed or produced substantially without interruption. Examples of industries employing continuous manufacturing processes are, for example, the petrochemical industry (e.g., oil and gas) or the float glass industry.

One difference between batch production and continuous production is that for continuous manufacturing processes the chemical transformations of input materials are made in substantially continuous reactions occurring in flowing streams of materials, while in batch processing, chemical transformations are performed discretely, e.g., in containers or chambers.

In the semiconductor device manufacturing industry, device manufacturers have managed to transition to more closely toleranced process and materials specifications by relying on process tool manufacturers to design better and/or faster process and hardware configurations. However, as device geometries shrink to the nanometer scale, complexity in manufacturing processes increases, and process and material specifications become more difficult to meet.

A typical process tool used in current semiconductor manufacturing can be described by a set of several thousand process variables. The variables are generally related to physical parameters of the manufacturing process and/or tools used in the manufacturing process. In some cases, of these several thousand variables, several hundred variables will be dynamic (e.g., changing in time during the manufacturing process or between manufacturing processes). The dynamic variables, for example, gas flow, gas pressure, delivered power, current, voltage, and temperature change based on, for example, a specific processing recipe, the particular step or series of steps in the overall sequence of processing steps, errors and faults that occur during the manufacturing process or changes in parameter values based on use of a particular tool or chamber (e.g., referred to as "drift").

Similarly, in pharmaceutical and biotech production, regulatory agencies such as the U.S. Food and Drug Administration require compliance with strict specifications on the manufacturing processes to maintain high quality products with very small variation around a specified quality profile. These specifications necessitate on-line measuring of process variables and additional multidimensional sensor techniques such as, for example, process gas chromatography, near-infrared spectroscopy, and mass spectroscopy. Ideally, data measured during manufacturing processes are available for real-time analysis and/or correction to provide indications or information concerning how close the process conditions are to the process specifications and to correct for deviations from specification.

Regulatory agencies often require manufacturers to demonstrate a process is maintained within a certain "knowledge space," where the knowledge space includes an operating region that has been explored through experimentation and/or mechanistic knowledge. For example, in the pharmaceutical and biotechnology industries, this concept is known as "Quality by Design" or "QbD." The knowledge space can also be referred to as the "design space" and generally includes an operating region that has produced products that have been verified to meet a specified quality standard.

Process variables are frequently related to yield or response variables. The process variables can be thought of as predictors or indicators of the yield or response variables based on an underlying relationship between the variables. Data indicative of the process and yield variables are measured and stored during a manufacturing process, either for real-time or later analysis.

Generally, two categories of data are associated with a manufacturing process. One type of data, usually denoted X-type data (e.g., X data, X-variables, X sets, or observation-level data), are indicative of factors, predictors, or indicators. X-type data are used to make projections or predictions about, for example, the manufacturing process or results of the manufacturing process. Another type of data, usually denoted Y-type data (e.g., Y data, Y-variables, Y sets), are indicative of yields or responses of the manufacturing processes. X-type data and Y-type data are generally related. Often the exact relationship between the X-type data and Y-type data are uncertain or difficult or impossible to determine. The relationship can, in some instances, be approximated or modeled by various techniques (e.g., linear approximation, quadratic approximation, polynomial fitting methods, exponential or power-series relationships, multivariate techniques (such as principal component analysis or partial least squares analysis) among others). In such cases, the relationship between X-type data and Y-type data can be inferred based on observing changes to both types of data and observing the response such changes cause to the other set of data.

One way to analyze and control manufacturing processes is known as "statistical process control" ("SPC") or "multivariate statistical process control" ("MSPC"). Generally, the statistical process control method is an open loop process in which a system provides multivariate-based monitoring of a manufacturing process to determine whether the process is operating normally. The system monitors the manufacturing process to determine whether the output product meets standards, whether the process operates consistently with past desirable operation, or other monitoring criteria. When the statistical process control system detects a deviation from normal operation, an alarm is triggered signaling the deviation to an operator or process engineer. The operator or process engineer interprets the alarm and determines the underlying cause of the deviation. The operator or engineer then manually takes corrective action to return the manufacturing process to normal operating conditions. One drawback of SPC or MSPC processes is the requirement that a process engineer or operator diagnose a problem and manually implement corrective steps.

Moreover, existing statistical process control methods are more difficult to apply to batch processes. Control over batch manufacturing processes involves monitoring a process and maintaining the process (e.g., by adjusting process parameters) along a trajectory that corresponds to a desirable result for the batch. This approach to applying multivariate control strategies to batch processes attempts to optimize a batch-level score space, and then determine the process trajectory that results in the optimized score space.

SUMMARY

Drawbacks of previous approaches include downtime associated with the process engineer receiving and interpreting the alarm and then deciding on and implementing corrective action. The concepts described herein involve a closed loop process for controlling the manufacturing process, based on a model (e.g., a predictive model). The predictive model is incorporated into a system or method to detect and identify faults in the manufacturing process and automatically manipulate or control the manufacturing process to maintain desirable operating parameters. Using the model-predictive concepts described here allow automated control over batch processes, e.g., by adjusting batch trajectories during processing to control or optimize the result of the batch process. Conceptually, the approach described here adds a layer of multivariate control (e.g., automated control) above and beyond process monitoring. Thus, in addition to detecting and diagnosing potential issues in the process, the method, system, and controllers described here can implement corrective action (e.g., by modifying operating parameters of the process) substantially in real-time via a closed loop process, resulting in higher and more consistent quality, less culled or scrapped materials or final products, less downtime, and less opportunity for human error.

The concept of "Quality by Design" promotes the use of control methods that adjust process conditions to assure desirable and consistent quality. Traditional model-based control methods are not suitable for batch manufacturing processes and are not designed to constrain a batch process within a design space, hence the these control methods manipulate the manufacturing process into new, unexplored operating regions that are outside the design or knowledge space. The concepts described here overcome this obstacle by monitoring closed-loop system performance and providing control actions in response that encourage or urge the manufacturing process towards the acceptable design or knowledge space, e.g., by appropriately analyzed and weighted constraints on the manufacturing process towards an acceptable model space (measured by, e.g., DModX). Using the model-predictive concepts described here allow automated control over batch processes, e.g., by adjusting batch trajectories during processing to control or optimize the result of the batch process.

An advantage realized is the avoidance of optimizing a batch-level score space and then imputing a trajectory to produce the optimized result. Instead, the systems and methods described determine a set of manipulated variable values that result in an optimized result at the completion of batch processing. To achieve tighter control, manipulated variables and manipulated variable data are distinguished from dependent variables and dependent variable data. The distinction between variable types facilitates analysis and determination of dependent variable trajectories as well as multivariate (e.g., DModX) statistics. In such configurations, disturbances in a multivariate (e.g., Hotelling $T^2$) and/or residual (e.g., DModX) space can be rejected substantially in real-time. The ability to reject variable changes that would result in a disturbance orthogonal to a multivariate space is a feature not present in systems that analyze data associated only with a score space.

Several features described herein provide further advantages as will be apparent to those of skill in the art. For example, multivariate statistical data are embedded in a model-based predictive control structure. The predictive control structure can provide expected values of certain types of data and statistics associated with the manufacturing process and control of the manufacturing process, for batch or continuous manufacturing processes. Moreover, observation-level control of continuous and batch processes is provided, and batch-level control of batch processes is provided (e.g., by adapting or configuring parameters of the multivariate model to the particular type of manufacturing process). For observation-level control (e.g., for either continuous or batch processing) and batch-level control (e.g., for batch processing), multivariate methods for estimating future values of dependent variables (and/or manipulated variables) are used to account for past, present, and/or future values of those variables and adapt or adjust the manufacturing process based on the results of predicted future changes. Multivariate (e.g., Hotelling's $T^2$ or DModX) statistics or values (e.g., scores or t-scores) are provided and/or predicted. Moreover, multivariate methods for estimating future values of dependent values are also described.

An additional advantage results from partitioning or dividing the X-type variables into subsets or sub-types. One subset of X-type data are identified as manipulated variables (or manipulated variable values) and denoted $X_{MV}$. Another subset of X-type data are identified as dependent variables and denoted $X_D$. Manipulated variables are generally variables or manufacturing parameters that can be directly controlled such as, for example, supplied temperature, chemical concentrations, pH, gas pressure, supplied power, current, voltage, or processing time. In general, a manufacturer usually accounts for or monitors less than about 20 manipulated variables due to processor and memory limitations in monitoring and analytical systems. Processes involving more than about 20 manipulated variables can become computationally unwieldy. Dependent variables are generally variables that are measured by sensors and cannot be controlled directly. Examples of dependent variables are, for example, chamber temperature, gas pressure, temperature or pressure gradients, impurity levels, spectral and/or chromatographic profiles, and others. Additionally, the dependent variables can represent a reduced data set (e.g., variables derived from raw data, such as differential temperature, temperature gradients, and others). Generally, dependent variables cannot be directly adjusted during the manufacturing process. Dependent variables can be related to, associated with, or dependent on the values of the manipulated variables, e.g., either via known relationships or unknown relationships which may or may not be empirically determinable and/or modeled.

In one aspect, the invention relates to a computer-implemented method for controlling a manufacturing process. The method involves receiving dependent variable data measured during the manufacturing process. The dependent variable data are representative of values of a first set of process parameters observed by one or more sensors. The method involves receiving manipulated variable data measured during the manufacturing process from a plurality of process tools and receiving predicted manipulated variable data.

Manipulated variable data are representative of a second set of process parameters (e.g., controllable or controlled process parameters). The method involves determining at least one of a predicted score value, a multivariate statistic, or both, based on at least the received data. The method also involves determining operating parameters of the manufacturing process based on at least the predicted score value, the multivariate statistic, or both.

In some embodiments, the second set of process parameters (e.g., which are represented by manipulated variable data) are controlled during the manufacturing process. The first set of process parameters (e.g., which are represented by dependent variable data) are not directly controlled during the manufacturing process. When the operating parameters include values for the manipulated variables, the method involves providing the manipulated variable values to the plurality of process tools. The method can also involve modifying the present or future values of the manipulated variables based on the past or present values of the manipulated variables and of the dependent variables.

Some embodiments of the method feature receiving predicted values for the dependent variable data. The method also involves, in some implementations, predicting values of the dependent variable data. Determining operating parameters can involve satisfying a controller objective. Examples of satisfying a controller objective include optimizing an operational objective function associating values of process data, yield data, result data, or any combination of these of the manufacturing process. The objective function can include one or more constraints on the dependent variable data, the manipulated variable data, the predicted score value, the multivariate statistics, or any combination of these. In some embodiments, the one or more constraints are user-specified. Constraints can be associated with penalties for deviating from a multivariate model.

Suitable controller objectives include, among others, a quadratic-type function. In such embodiments, satisfying the controller objective includes minimizing a parameter of the objective function. Some implementations involve determining desirable values of the score or the multivariate statistic (or statistics). In some embodiments, the method involves using a dependent variable model that predicts values of predicted dependent variable data based on determined values of the manipulated variable data, the past or present values of the dependent variable data, or combinations of these.

In some embodiments, the method involves using a score model that predicts future values of the first set of process parameters (e.g., which are represented by dependent variable data) and the second set of process parameters (e.g., which are represented by manipulated variable data). The method can involve determining, with a multivariate model, the predicted value for the score, the one or more multivariate statistics, or both. Some implementations feature the multivariate model receiving measured manipulated and dependent variable data and predicted manipulated and dependent variable data.

Examples of suitable multivariate statistics for use in the method include one or more of the following: a score, a Hotelling's $T^2$ value, a DModX value, a residual standard deviation value, or any combination of these. The multivariate statistic can also include a principal components analysis t-score or a partial least squares t-score, or both. The manufacturing process can be a continuous-type or a batch-type manufacturing process.

In another aspect, the invention relates to a multivariate controller for a continuous or batch-type manufacturing process. The controller includes a control module in communication with a plurality of process tools and a plurality of sensors to monitor manipulated variable data from the process tools and dependent variable data from the sensors. The control module includes a multivariate model. The dependent variable data are representative of values of a first set of process parameters that are observed by the plurality of sensors. The manipulated variable data are representative of expected values of a second set of process parameters (e.g., controlled or controllable parameters). The controller also includes a solver module to receive, from the multivariate model, at least one of predicted yield data, predicted manipulated variable data, predicted dependent variable data, a multivariate statistic or any combination of these based on at least the monitored manipulated variable and dependent variable data. The solver module also generates values of the manipulated variables for providing to the plurality of process tools and to a prediction model that provides at least predicted statistical data.

The controller, in some implementations, adjusts one or more parameters of the plurality of process tools based on the generated values of the manipulated variables. The multivariate statistic used by the controller includes at least one of a score, Hotelling's $T^2$ value, a DModX value, a residual standard deviation value, or a combination of these. In some embodiments, the prediction model includes a score model to generate predicted values for the solver module of one or more multivariate statistics. The prediction model can include a dependent variable model to generate predicted dependent variable values. The prediction model can also provide predicted values of dependent variables from the manufacturing process. Some implementations feature the prediction model providing predicted statistical data to the control module and the solver module.

In some embodiments, the solver module generates values of the manipulated variables based on a controller objective. The controller objective can optimize a quadratic-type function associated with the manufacturing process. Some implementations involve a controller objective with one or more constraints on, e.g., the dependent variable data, the manipulated variable data, the predicted yield data, the multivariate statistic (or statistics), or some combination of these (or all of these). The constraints can be user-specified or associated with penalties for deviating from the multivariate model. In some embodiments, the solver module is a constrained optimization solver. Some configurations include the control module including the solver module. Moreover, the solver module can include the control module, or both the solver module and the control module can be sub-modules of a larger module, processor, or computing environment.

In general, in another aspect, the invention relates to a system for controlling a manufacturing process. The system includes a data acquisition means for acquiring, from a plurality of process tools, manipulated variable data representative of expected values of a set of process parameters and for acquiring, from a plurality of sensors, dependent variable data representative of values of a second set of process parameters observed by the plurality of sensors. The system includes a process control means for determining operational parameters of the plurality of process tools. The system also includes a multivariate control means to determine, based on a multivariate statistical model, values for the manipulated variable data to provide to the process control means. The multivariate statistical model receives at least the acquired manipulated variable data and dependent variable data and provides predicted yield values and statistical information to the process control means based on at least the received data.

In some embodiments, the operational parameters determined by the process control means optimize or satisfy a control objective.

Some implementations include any of the above-described aspects featuring any of the above embodiments or benefits thereof.

These and other features will be more fully understood by reference to the following description and drawings, which are illustrative and not necessarily to scale. Although the concepts are described herein with respect to a manufacturing process, particularly a semiconductor, pharmaceutical or biotechnical manufacturing process, it will be apparent to one of skill in the art that the concepts have additional applications, for example, metallurgic and mining applications, financial data analysis applications, or other applications involving a large number of data points or observations.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1:
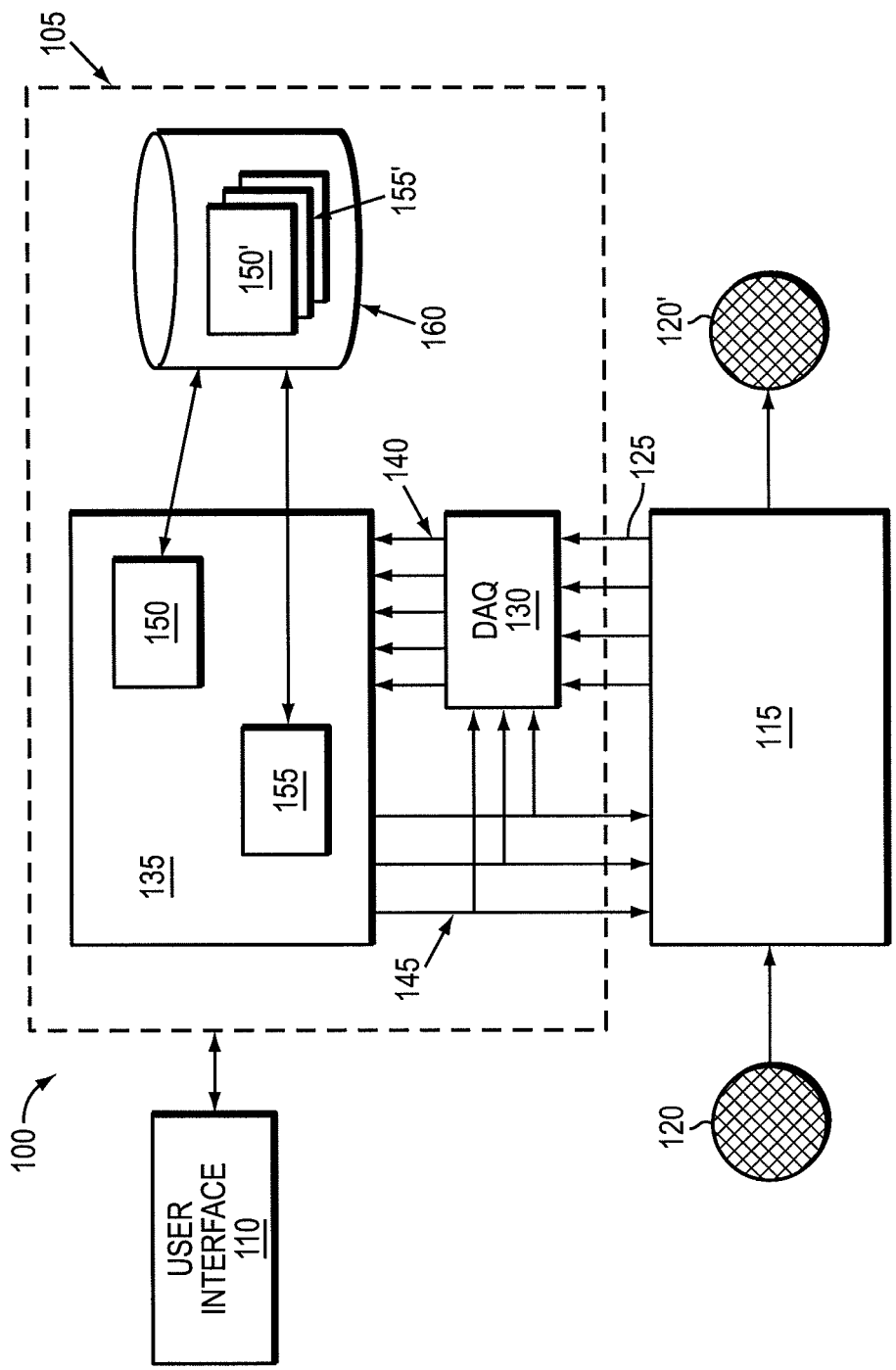
FIG. 1 is a block diagram of a system that embodies aspects of the invention.

FIG. 1 depicts an exemplary system 100 that includes a processor 105 and a user interface 110. The user interface 110 can include a computer keyboard, mouse, other haptic interfaces, a graphical user interface, voice input, or other input/output channel for a user to communicate with the processor 105 in response to stimuli from the processor 105 (e.g., to specify values for constraints). The user interface 110 can include a display such as a computer monitor. The processor 105 is coupled to a processing facility 115. The processing facility 115 performs manufacturing or processing operations. For example, in the context of the semiconductor industry, the processing facility performs processing functions on a wafer 120 and outputs a processed wafer 120'. The wafer 120 and processed wafer 120' are illustrative only, and can represent any input and/or output of a batch-type manufacturing process (e.g., a pharmaceutical granulation or blending or other unit processing step, or biotechnology fermentation, cell culture, or purification process). The processing facility 115 can include tools or processes (not shown) for, for example, cleaning, purification, depositing material, mixing materials or chemicals, dissolving materials or chemicals, removing materials, rinsing materials, and/or performing other functions within the processing facility 115.

In some embodiments, the tools or processes include multiple stations or units within the facility 115. These functions can be associated with a plurality of physical parameters, for example, gas pressure, gas flow rate, temperature, time, and/or plasma or chemicals or biochemical concentrations, among many others. In some embodiments, the parameter is the yield loss of the particular wafer 120 that occurs after processing. The physical parameters can be monitored and manipulated to produce a plurality of outputs 125 containing data about the variables (e.g., the physical parameters and/or tool operating conditions) in the processing facility 115. The outputs 125 can be electrical, optical, magnetic, acoustic, or other signals capable of transmitting the data or being transmitted to or within the processor 105. The outputs 125 can include data representative of dependent variable data $X_D$, manipulated variable data $X_{MV}$, or both. In some embodiments, the outputs 125 provide raw data that can be manipulated before being used as dependent variable data or manipulated variable data.

The processing facility 115 is coupled to the processor 105 by a data acquisition module 130. The data acquisition module 130 receives the outputs 125 from the processing facility 115. In some embodiments, the data acquisition module 130 performs buffering, multiplexing, signaling, switching, routing, formatting, and other functions on the data to put the data in a format or condition for suitable communication or retransmission to other modules of the processor 105.

The system 100 also includes a controller module 135. The controller module 135 receives data from the data acquisition module 130, e.g., via communication links 140. The controller module specifies manipulated variable data $X_{MV}$ and communicates the specified values to the processing facility 115 and the data acquisition module 130 via a plurality of outputs 145. The manipulated variable data can represent setpoint values of particular processing parameters (e.g., temperature, gas flow rate, pressure, processing time, and others) or instructions for particular process tools. The controller module 135 includes a multivariate model 150 and a prediction model 155. The multivariate model 150 is used, in conjunction with other modules of the controller module 135 (e.g., a solver module (not shown)), to determine values of operating parameters or manipulated variables that produce desirables values of dependent variable data (e.g., data within an acceptable knowledge space for the particular manufacturing process). The prediction model 155 is used to predict multivariate statistics, scores, and variable values for use in conjunction with other modules of the controller module 135.

The particular processes that occur within the processing facility 115 can be monitored or controlled by the processor 105 via the controller module 135. The controller module 135 monitors and controls the processing facility 115 by comparing the ideal values of manipulated variable data with the values used by processing tools within the facility 115 or the facility 115 itself and by comparing ideal values of dependent variable data with the values measured by sensors. The actual values of the processing parameters within the processing facility 115 are measured by and/or communicated to the data acquisition module 130 by the plurality of outputs 125.

The system 100 also includes a memory 160. The memory 160 can be used for, for example, storing previously-generated multivariate models 150' and/or previously-generated prediction models 155' for later use.

Figure 2:
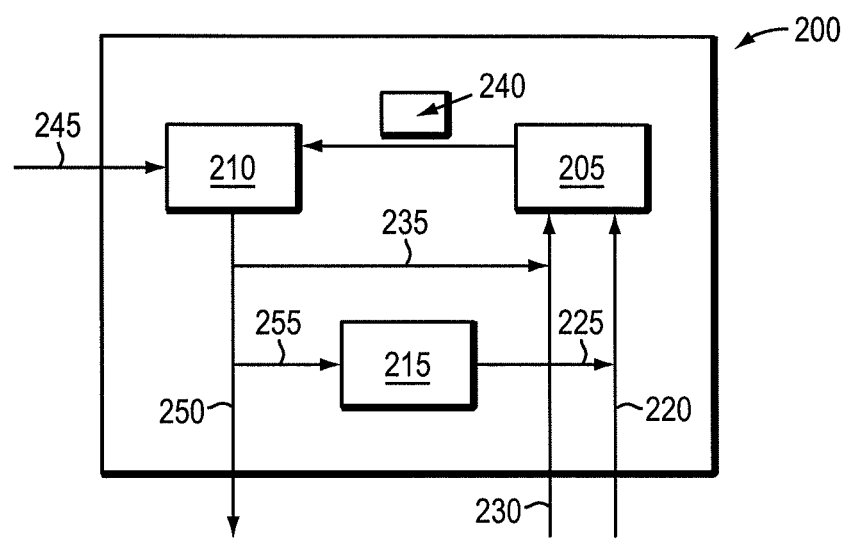
FIG. 2 is a block diagram illustrating an embodiment of a controller that includes a multivariate model.

FIG. 2 is a block diagram illustrating an embodiment of a controller 200 that includes a multivariate model 205. The controller 200 also includes a solver module 210 and a dependent variable $X_D$ model 215.

The multivariate model 205 receives as input dependent variable data 220 from a plurality of sensors (not shown). The dependent variable data 220 can be expanded by predicted dependent variable values 225 provided from the dependent variable model 215. The multivariate model 205 also receives measured values of manipulated variable data 230. The multivariate model 205 also receives manipulated variable data 235 from the solver module 210.

The multivariate model 205 receives measured (220) and predicted (225) values for the dependent variable data as well as measured (230) and predicted (e.g., setpoint values) (235) values for the manipulated variable data. Based on the received data, the multivariate model 205 provides information 240 to the solver module 210. The information 240 can include, e.g., a score and one or more multivariate statistics. For example, the score can be a predicted yield score ($Y_{pred}$). The predicted yield score $Y_{pred}$ is similar to the scores provided in statistical process control without a multivariate model (e.g., the predicted yield score can be based on a principal component analysis or partial least squares calculation). The one or more multivariate statistics can include a Hotelling $T^2$ value or a DModX value. Similarly, the one or more multivariate statistics can include a residual standard deviation value, a principal component analysis score, a partial least squares (sometimes called projection to latent structures) score, or any combination of the multivariate statistics discussed here. In some embodiments, the information 240 includes provides more than one multivariate statistic to the solver module 210. The multivariate statistics can provide constraints to the solver module 210.

The multivariate model 205 can perform, for example, a Hotelling calculation or a DModX calculation on the received data by means of a principal components or partial least squares analysis to determine a $T^2$ or DModX value, respectively. A $T^2$ value can be calculated according to the following equation:

$$T^2 = \left(\frac{\bar{x} - \mu_0}{\sigma}\right)^T S^{-1} \left(\frac{\bar{x} - \mu_0}{\sigma}\right)$$

where:
σ=standard deviation for a particular variable, based on data acquired for previous batches, $$\bar{x} = \begin{bmatrix} \bar{x}_1 \\ \bar{x}_2 \\ \vdots \\ \bar{x}_p \end{bmatrix},$$

measured value of variables, for p variables, $$\mu_0 = \begin{bmatrix} \mu_1^0 \\ \mu_2^0 \\ \vdots \\ \mu_p^0 \end{bmatrix},$$

mean value of variables based on previous batches, for p variables, $S^{-1}$=an inverse covariance or correlation matrix, which is the inverse of the covariance or correlation matrix, S, illustrated below:

$$S = \begin{bmatrix} \bar{S}_1^2 & \bar{S}_{12} & \bar{S}_{13} & \cdots & \bar{S}_{1p} \\ & \bar{S}_2^2 & \bar{S}_{23} & \cdots & \bar{S}_{2p} \\ & & \bar{S}_3^2 & \cdots & \bar{S}_{3p} \\ & & & \ddots & \vdots \\ & & & & \bar{S}_p^2 \end{bmatrix}$$

where:

$$S_{ij} = \frac{1}{N-1} \sum_{i=1}^{k} \sum_{j=1}^{n_i} (x_{ij} - \bar{x})(x_{ij} - \bar{x})^T,$$

where indices i and j identify the matrix element for both S and x in a generalized k×n matrix.

In the multivariate modeling example above, the x-variables in the above equations usually are score vectors of a principal components or partial least squares model usually with mean values ($\mu_0$) equaling zero. Because these score vectors are orthogonal, the matrices S and $S^{-1}$ are diagonal with the variances and respective inverse variances of each component score vector as diagonal elements.

A t-score value can be thought of as a projection onto a line (e.g., a principal components or partial least squares model axis) in a p-dimensional space that provides an acceptable approximation of the data (e.g., a line that provides an acceptable least squares fit). A second t-score can be used (e.g., a projection onto a line orthogonal to the first line) in some embodiments.

In general, a $T^2$ value is a calculation of the weighted distance of manufacturing process variables for an output (e.g., the wafer 120') of the manufacturing process relative to an output produced under normal process operation or based on predicted values of dependent variable data and/or manipulated variable data. One way to understand the meaning of the $T^2$ value is to consider it in terms of a geometric description. A normal manufacturing process is a cluster of data points in an p-dimensional space, where p is the number of measured manufacturing process variables. The pertinent space can also be the reduced dimensionality space of the scores. Hotelling's $T^2$ value is the squared distance of a new output from the center of this cluster of data points weighted relative to the variation output of the in the normal process condition. The variation is often illustrated as an p-dimensional hyper-ellipse that bounds the cluster of data points. In general, Hotelling-type calculations can be used to, for example, determine whether a particular point is an outlier (e.g., outside the hyper-ellipse) with respect to the remainder of the data set. More specifically, a Hotelling calculation can be used to determine whether a particular measured parameter is outside an alarm limit or outside the knowledge space, as determined by a mathematical model for the process parameters being observed.

Another example of a multivariate statistic is a DModX calculation or residual standard deviation calculation. A DModX calculation involves calculating the distance of a particular data point from a location in an p-dimensional space that represents a preferred location (e.g., a location associated with an ideal batch). The DModX value is calculated using a principal components or partial least squares analysis that maps the p-dimensional variable to a lower order (e.g., less than order p) dimensional variable (e.g., a score space). Mathematically, the DModX value is the orthogonal component (or residual) resulting from the principal components or partial least squares analysis. A DModX value can be indicative of a range of values (e.g., a "tolerance volume") about one or more variables (e.g., data points) in the mathematical model.

The solver module 210 also receives operational objective values 245 representing the target or setpoint value of quality, yield, process variable or multivariate limit or targets. The solver module 210, based on the received information 240 and operational objective values 245, determines values of the manipulated variable values 250 to provide to a plurality of process tools (not shown). The determined manipulated variables values 250 are also an input to the multivariate model 205 (e.g., manipulated variable values 235) and an input 255 to the dependent variable model 215. In some embodiments, the manipulated variable values 250 represent setpoint values of the manipulated variables for the manufacturing process that can differ from the measured manipulated variable values 230 (e.g., the present value of the manipulated variables).

In some embodiments, the solver module 210 performs a search for manipulated variable values that satisfy some controller objective. The solver module 210 is constrained in this search by the information 240 the multivariate model 205 provides and the multivariate limits expressed in the operational objective values 245. In some embodiments, a user specifies additional constraints on the solver module 210 (e.g., using the user interface 115 of FIG. 1).

The dependent variable $X_D$ model 215 provides predicted values 225 of dependent variable data to the multivariate model 205. The dependent variable model 215 can provide predicted values of dependent variable data in a variety of ways. For example, the predicted value can be an average value of measured dependent variables over time or an average trajectory of dependent variable values over time. The predicted values can be an average value or trajectory plus some allowance value (e.g., $\Delta X_D$).

In some embodiments, dependent variable data are a function of manipulated variable data such that the value of a particular dependent variable functionally depends on the value of one or more manipulated variables (e.g., $X_D=f(X_{MV})$). The functional relationship can be known or empirically inferred, determined, or modeled. In embodiments in which dependent variable data are functionally related to the manipulated variable data, the controller 200 can implement an iterative solution to variations from the expected dependent variable values, whereby a closed-loop process is used to adjust values of the operating parameters associated with the manipulated variables to more closely approximate the desired values of the dependent variables.

The controller 200 facilitates modification of the present values (235) or future values (250) of manipulated variable data based on the past values (220) or present values (225) of dependent variables or past values (230) or present values (235) of the manipulated variables.

The frequency of modifications to the manipulated variables can depend on, for example, the type of control or the type of processing (e.g., batch-type or continuous-type). For example, for observation-level control of batch processes (e.g., control of each step in a processing recipe), the controller 200 can facilitate relatively frequent adjustment to the operating parameters represented by the manipulated variable data to maintain observation-level scores (e.g., t scores) and to maintain the value of DModX (e.g., maintaining design space control). For batch-level control of batch processes (e.g., control of the output of a batch process), the controller 200 can facilitate relatively fewer adjustments to the operating parameters. The fewer adjustments can be coordinated based on or according to predetermined times during the manufacturing process to maintain or optimize certain scores or multivariate statistics (e.g., $Y_{pred}$, scores, $T^2$, and/or DModX), as well as desirable values of yield or other quality result variables.

Figure 3:
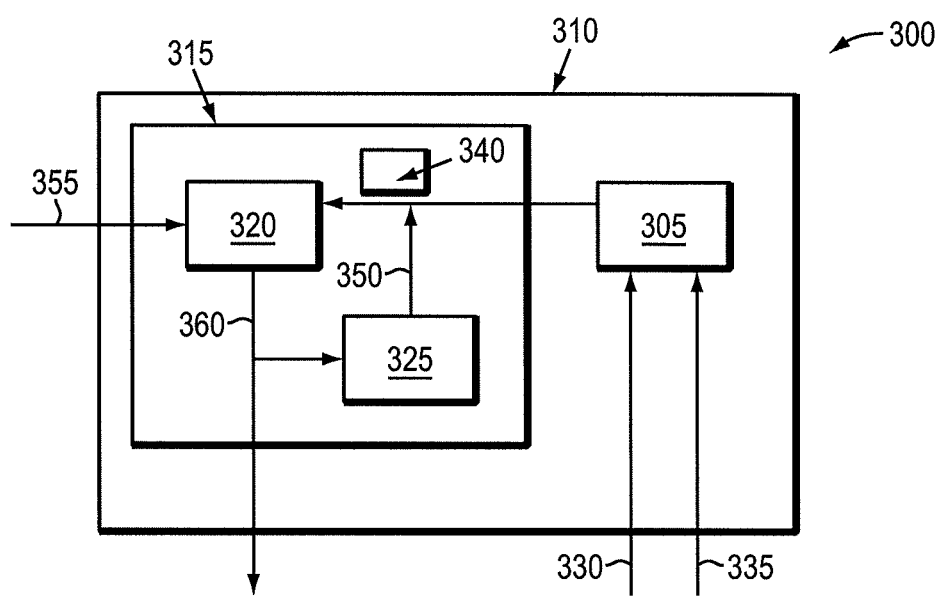
FIG. 3 is a block diagram illustrating another embodiment of a controller that includes a multivariate model.

FIG. 3 is a block diagram illustrating another embodiment of a controller 300 that incorporates a multivariate model 305. The controller 300 includes a control module 310. The control module 310 includes the multivariate model 305 and a control sub-module 315. The control sub-module 315 includes a solver module 320 and a score model 325. The controller 300 is a simplified version of the controller 200 of FIG. 2. In some embodiments, the controller 300 does not constrain the multivariate model 305 to particular values of DModX.

The multivariate model 305 receives manipulated variable values 330 from a plurality of process tools (not shown) and dependent variable values 335 from a plurality of sensors (not shown). Based on the received data, the multivariate model 305 calculates and provides information 340 to the solver module 320. The information 340 can include, for example, a t-score and predicted yield values. The predicted yield values can be based on, for example, a partial least squares calculation. The information 340 can include a predicted score value 350 from the score model 325. The solver module 320 also receives a setpoint or target value for yield data 355.

Based on the received data (340, 355), the solver module 320 calculates manipulated variable values 360. The calculated manipulated variable values 360 are provided to the score model 325 and a plurality of process tools (not shown). In calculating the manipulated variable values, the solver module 320 performs a search of manipulated variable values that satisfy a controller objective. The controller objective can include, for example, constraints and/or penalties. In some embodiments, the controller objective is a quadratic controller objective. Other objective functions will be apparent to those of skill.

The score model 325 calculates and produces predicted score values based on, for example, past and present manipulated variable values. The score model 325 also produces predicted score values based on, for example, future estimated scores resulting from adjusted manipulated variable values. For example, the score model can include and account for the relationship between changes in scores based on changes in manipulated variable values ($\Delta t_i=f(\Delta X_{MVi})$) as well as the relationship between score values and predicted yield values ($Y_{pred}=f(t)$). Like the controller 200 of FIG. 2, the controller 300 provides manipulated variable values (e.g., setpoint values for operating parameters of the manufacturing process) to a plurality of process tools for subsequent processing.

Figure 4:
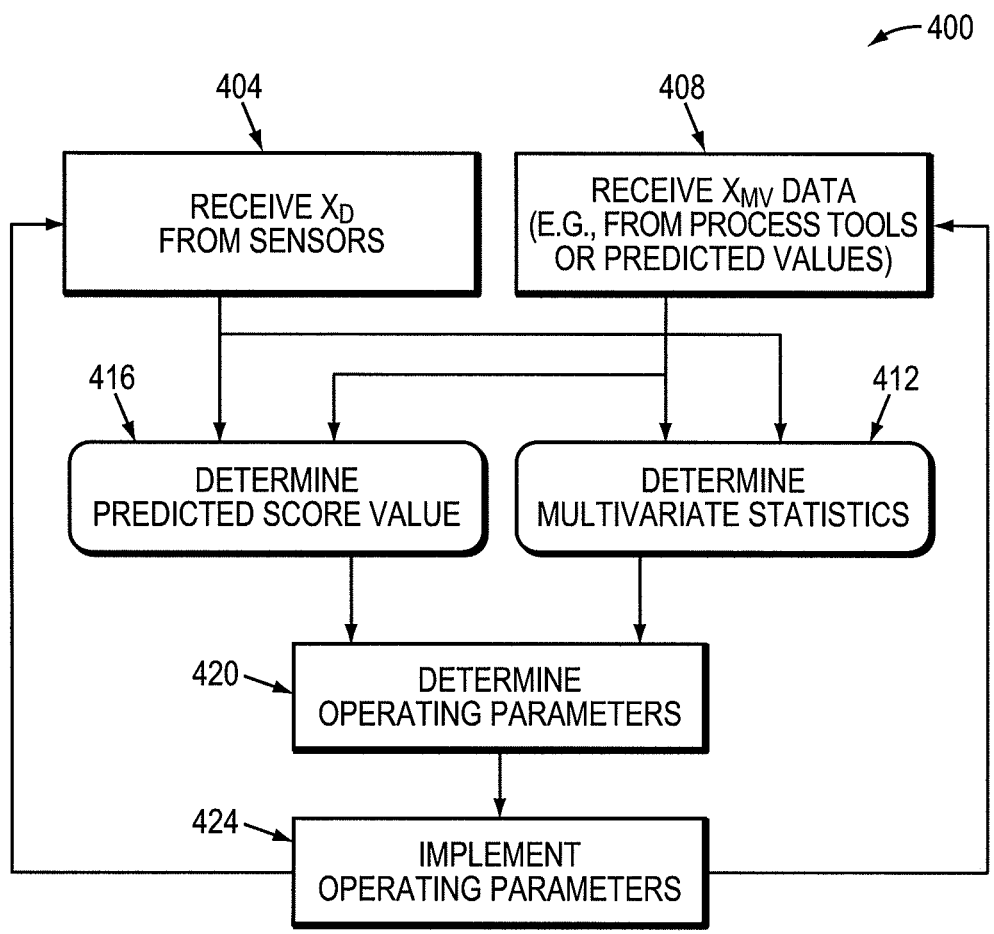
FIG. 4 is a flow chart illustrating a method for implementing operating parameters for a manufacturing process.

FIG. 4 is a flow chart 400 illustrating a method for implementing operating parameters for a manufacturing process. The method depicted in the flow chart 400 can be implemented by, for example, the controller 200 of FIG. 2 or the controller 300 of FIG. 3. In step 404, dependent variable data ($X_D$) is received from a plurality of sensors used in the manufacturing process. The dependent variable data can be associated with batch-type processes or continuous-type processes. In step 408, manipulated variable data ($X_{MV}$) is received, e.g., either from a plurality of process tools from a prediction model, or both.

From the received data, multivariate statistics are determined (step 412), and predicted variable values ($Y_{pred}$) can be determined (step 416). In some embodiments, the multivariate statistics are calculated by a multivariate model. Examples of such statistics include scores, Hotelling $T^2$ values, DModX values, residual standard deviation values, principal components scores, partial least squares scores, some combination of these, or all of these statistics. In some embodiments, the statistics are constrained by, for example, user-specified constraints, tolerance levels, or threshold values. The predicted variable values can be determined (step 416) based on past, present, and future values of manipulated variables and past and present values of dependent variables. In some embodiments, the predicted variable values are based on predicted future values of dependent variables.

At step 420, a set of operating parameters are determined. In some embodiments, the set of operating parameters are represented by a set of manipulated variable data to be supplied to a plurality of process tools. The manipulated variable data can be setpoint or target values of manipulable or controllable variables. In some embodiments, the manipulated variable data can be adjustments to the setpoint or target values of manipulable or controllable variables (e.g., to recalibrate or encourage the dependent variables to converge on desirable values). After the operating parameters (e.g., manipulated variables) are determined (step 420), the operating parameters are implemented (step 424) by, for example, communicating the new setpoint or target values to the plurality of process tools. The process tools can be automatically or manually adjusted based on the determined values.

Figure 5:
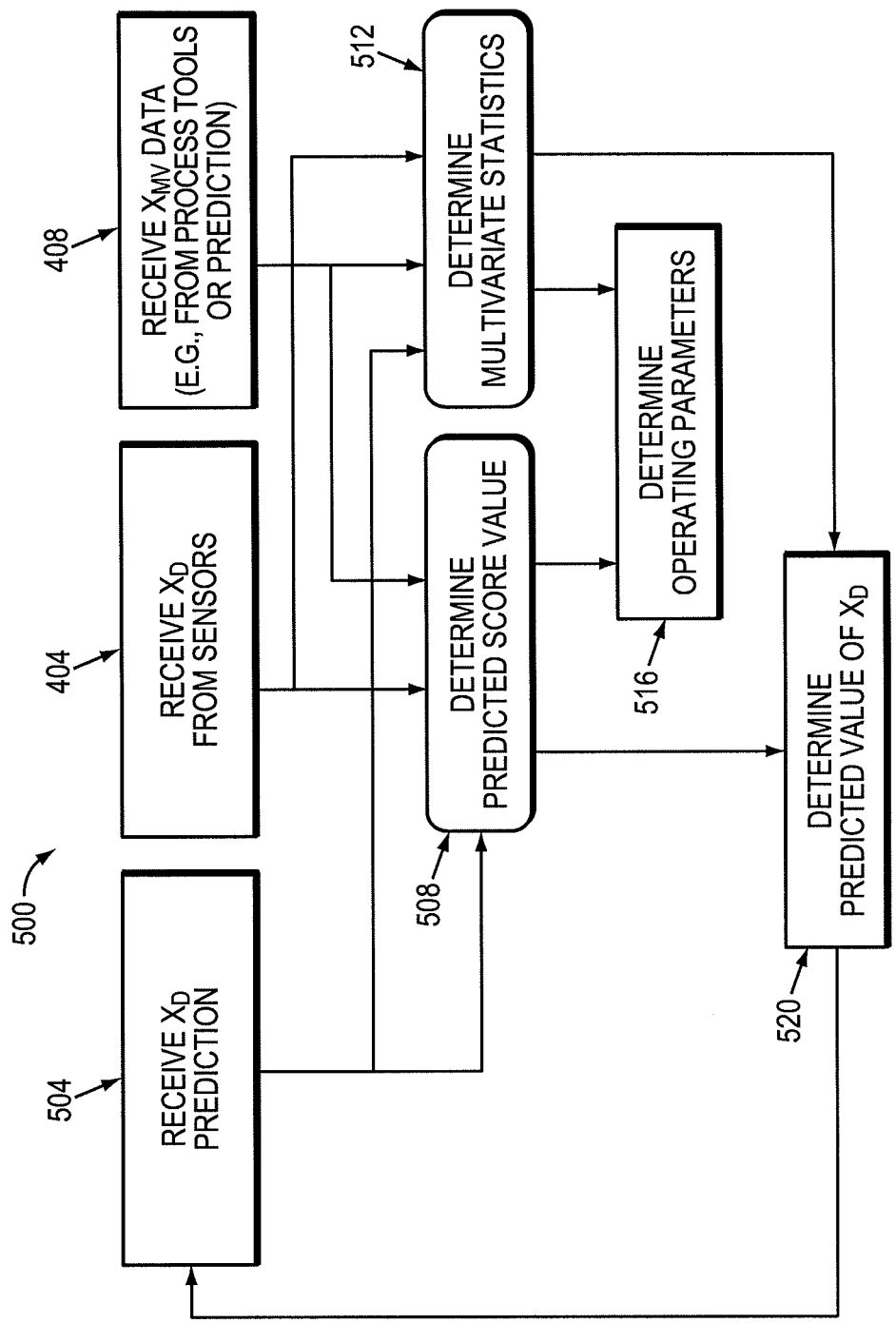
FIG. 5 is a flow chart illustrating a method for determining operating parameters for a manufacturing process and for determining a predicted value of dependent variable data.

FIG. 5 is a flow chart 500 illustrating a method for determining operating parameters for a manufacturing process and for determining a predicted value of dependent variable data. The flow chart 500 includes steps 404 and 408 of the method depicted in the flow chart 400 of FIG. 4. Specifically, at step 404 dependent variable data $X_D$ is received from a plurality of sensors. At step 408, manipulated variable data $X_{MV}$ is received, e.g., either from a plurality of process tools or from a prediction or both. At step 504, predicted values of the dependent variable data are received (e.g., from a dependent variable prediction model). Based on the received dependent variable data, received manipulated variable data, and the predicted variable data (step 508) and multivariate statistics (step 512) are determined.

The predicted process values and the multivariate statistics are used to determine operating parameters of the manufacturing process (step 516). In some embodiments, determining the operating parameters involves determining values for the manipulated variables and/or providing the determined values to a plurality of process tools to implement (e.g., by adjusting the setpoint values of the plurality of process tools). Moreover, the predicted variable values and the one or more multivariate statistics are used to determine a predicted value of the dependent variable data (step 520). The flow chart 500 represents an iterative process in which the determined predicted value of the dependent variable data from step 520 is provided at step 504. In some embodiments, the controller 200 of FIG. 2 performs the steps of the flow chart 500.

Figure 6:
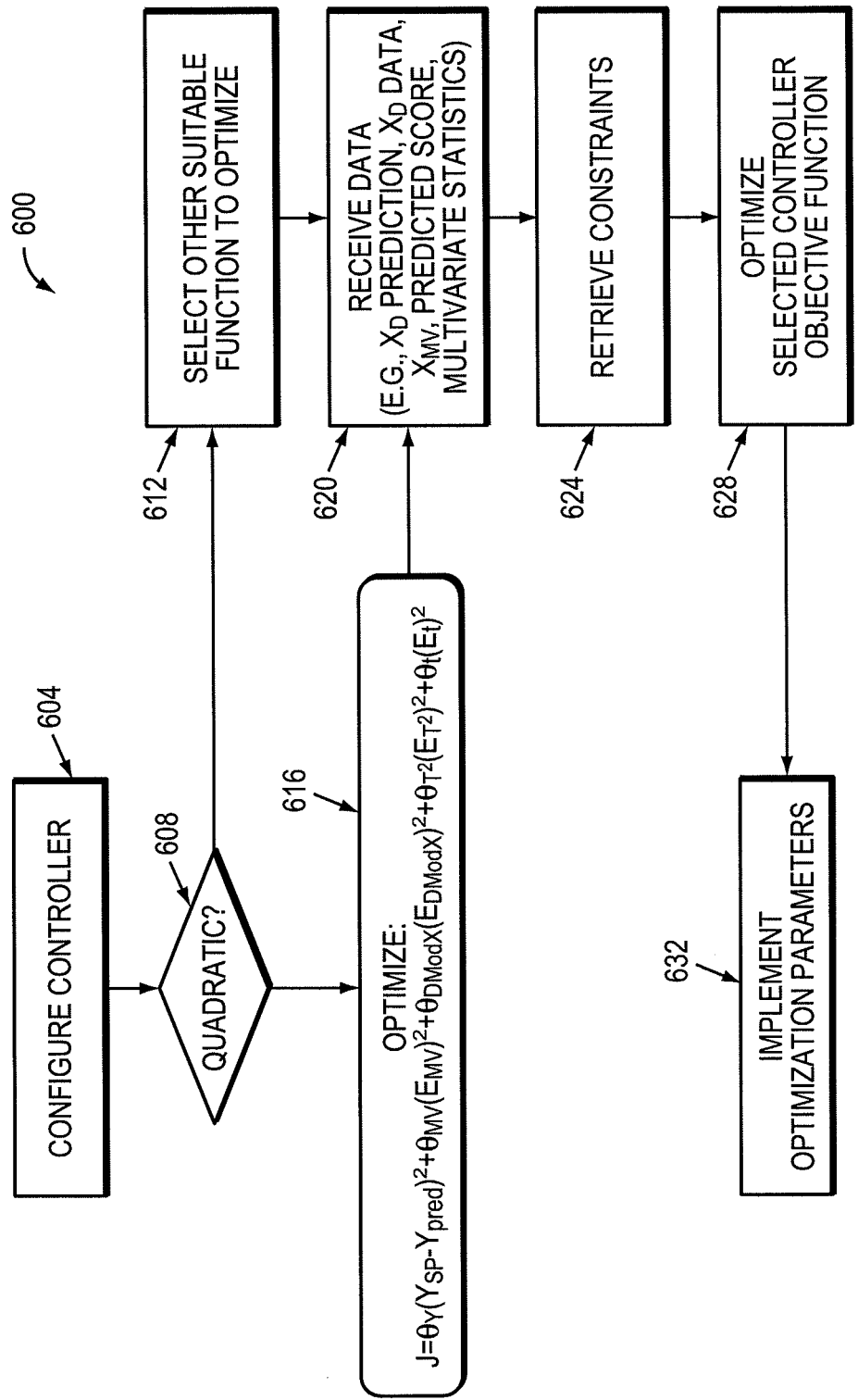
FIG. 6 is a flow chart illustrating a method for determining and implementing operational parameters for a manufacturing process.

FIG. 6 is a flow chart 600 illustrating a method for determining and implementing operational parameters for a manufacturing process. In step 604, a controller is configured. An example of a controller configuration is the type of objective function that is optimized. For example, at step 608 a query determines whether the controller objective is a quadratic-type control function. If the control objective is not a quadratic-type function, an alternative or complementary function to optimize is selected (step 612).

If a quadratic-type control function is selected at step 608, the process proceeds to step 616, which illustrates a quadratic-type control function to optimize. The objective function, J, that associates the received data, the constraints, and penalty values. In some embodiments, optimizing the quadratic-type objective function involves minimizing J over the value of the manipulated variable data $X_{MV}$.

The objective function J to be optimized is $$J = \theta_Y(Y_{SP} - Y_{pred})^2 + \theta_{MV}(E_{MV})^2 + \theta_{DModX}(E_{DModX})^2 + \theta_{T2}(E_{T2})^2 + \theta_t(E_t)^2$$

where:

$Y_{SP}$ = a setpoint or target value for Y data values (e.g., yield or quality);

$Y_{pred}$ = a predicted value for Y data values. In some embodiments, $Y_{pred}$ is determined by a partial least squares model or other suitable model based on $X_{MV}$, $X_D$, and $X_K$. $X_K$ represents the known past or present values of $Y_{SP}$, $Y_{pred}$, $X_{MV}$, and $X_D$ and $X_{MV}$ represents future values of the manipulated variables for control. For example, $Y_{pred} = f_Y(X_K, X_{MV}, X_D)$ where $f_Y$ is a modeling function;

$\theta_Y$, $\theta_{MV}$, $\theta_{DModX}$, $\theta_{T2}$, and $\theta_t$ are penalty weights;

$E_{MV}$ = a function relating an amount of deviation in the manipulated variables from a desired trajectory that is subject to the penalty weight $\theta_{MV}$. An example of $E_{MV}$ is $(X_{MV,R} - X_{MV})$;

$E_{DModX}$ = the amount of the DModX space that is subject to the penalty $\theta_{DModX}$;

$E_{T2}$ = the amount of the Hotelling $T^2$ score that is subject to the penalty $\theta_{T2}$;

Et = the portion of the scores, t, that are subject to the penalty $\theta_t$;

As discussed above, $T^2$ represents a distance of a multivariate system from its center point in the model hyperplane. The $T^2$ values are based on a function ($f_{T2}$) derived from a principal component analysis or partial least squares model and can be represented as $T^2 = f_{T2}(X_K, X_{MV}, X_D)$. DModX represents a deviation of the multivariate system from the model hyperplane. The DModX values are based on a function ($f_{DModX}$) derived from a principal component analysis or partial least squares model and can be represented as DModX = $f_{DModX}(X_K, X_{MV}, X_D)$. The t values are based on a function ($f_{ti}$) derived from a principal component analysis or partial least squares model and can be represented as $t_i = f_{ti}(X_K, X_{MV}, X_D)$, where $t_i$ represents the value of the ith score. The values of $X_D$ represent future values of dependent variables and are based on an appropriate function ($f_{XD}$) relating $X_K$ and $X_{MV}$, e.g., $X_D = f_{XD}(X_K, X_{MV})$. In some embodiments, $f_{XD}$ is a finite impulse response (FIR) model. The function $f_{XD}$ can also be an auto-regressive moving average model (ARMA). Other types of models of $f_{XD}$ will be apparent to those of skill.

In some embodiments, the objective function J is subject to default constraints. An example of a default constraint on manipulated variable data are shown below:

$$X_{MV_{min}} < X_{MV} < X_{MV_{max}}$$

Some implementations do not require all of the penalty weights discussed above. For example, if the user's objective is to maintain a system or process within the space of the multivariate model (e.g., for design-space control), the method can ignore the contributions of the Y variables (e.g., because no Y variables will be calculated). In such a case, the penalty $\theta_Y$ can be set to 0.

The values or functional representation of $E_{MV}$, $E_{DModX}$, and $E_{T2}$ can be determined according to a variety of methods.

For example, the $E_X$ term can be a sum of squared distances from a target or threshold. Specific implementations are discussed below, but it will be apparent to those of skill that other implementations are also possible.

$E_{MV} = \Delta X^T_{MV} \cdot \Delta X_{MV}$; where $\Delta X_{MV}$ is a vector representing changes or deviations in observed values of $X_{MV}$ from the particular processing recipe;

$$E_{T^2} = \sum_h \{MAX((T_h^2 - T_{h,max}^2), 0)\}^2;$$

where $T^2_{h,max}$ represents maximum values of $T^2$ threshold at h future points in time and $T^2_h$ represents values of $T^2$ at h future points in time; and $$E_{DModX} = \sum_h \{MAX((DModX_h - DModX_{h,max}), 0)\}^2;$$

where $DModX_{h,max}$ represents maximum values of DModX threshold at h future points in time and $DModX_h$ represents values of DModX at h future points in time.

At step 620, data are received. The data can include, for example, predicted dependent variable data, measured/received dependent variable data (e.g., from a plurality of process tools), measured or predicted manipulated variable data, predicted variable values, one or more multivariate statistics or any combination of these data types. The data can be used as an input for, for example, a solver module that determines manipulated variable values that satisfies a controller objective.

Additionally, the method involves retrieving one or more constraints (step 624) (e.g., from a memory or via a user interface). The constraints can be user-specified, or the constraints can be default or threshold values. In some embodiments, when a particular type of data are not received, the constraints associated with that type of data are not used. For example, if predicted dependent variable data are not received or used, constraints associated with predicted dependent variable data are disabled, unavailable, or not used, e.g., by the solver.

Step 628 involves a process of optimizing the selected controller objective function. Examples of suitable controller objective functions are quadratic-type functions, linear function or nonlinear function that penalizes operations that stray from the objective. For example, for batch processing, the control objective can vary, and as a result, the applicable objective function can also vary. For example, the control objective, for batch processing, can include optimizing an objective during a batch trajectory (or throughout the batch trajectory), optimizing the final batch condition (e.g., yield, quality, or other metrics of successful processing), or a combination of these objectives. In some embodiments, the particular constraints and/or penalties used or values ascribed to the penalties or constraints can vary depending on the particular objective.

After the function is optimized at step 628, the optimization parameters are determined and implemented (step 632). For example, the optimization parameters can result in a set of values or adjustments for the manipulated variable data, and the values or adjustments are communicated to a plurality of process tools. The process tools are then manually or automatically updated or confirmed based on the provided manipulated variable data.

The concepts described herein are applicable to both continuous-type manufacturing processes and also to batch-type manufacturing processes. Generally, for continuous-type manufacturing processes, the correlation of process measurements to target or setpoint values does not drastically change over time during normal operating conditions. Thus, for continuous processes, implementing control with a multivariate model incorporates penalties on certain multivariate statistics such as t values, $T^2$ values, and DModX values. The values for these multivariate statistics are determined based on values of $X_K$, $X_{MV}$, and $X_D$. As discussed above, $X_K$ represents known past and present values of system parameters (e.g., past and present values of $X_{MV}$ and $X_D$). The values of $X_{MV}$ represent future values of the manipulated variables, and $X_D$ represents future values of dependent variables. Thus, the control method and system can account for the impact of future changes in operating parameters on manipulated variable values and dependent variable values before changes or adjustments are implemented.

In continuous-type manufacturing processes, future values for dependent variables (e.g., $X_D$ values) can be estimated or predicted using multivariate process control techniques such as finite impulse response (FIR) or auto-regressive moving average (ARMA) models as discussed above. In some embodiments, system and method incorporate a prediction horizon that provides stability to closed loop response of the method. A prediction horizon can include estimates of conditions of the particular manufacturing system at more than one point in time in the future.

In batch-type manufacturing processes, the objective function J can also be used. In some embodiments for batch-type manufacturing processes, the types of multivariate model used, how data are organized/stored/processed, and the prediction of future values of $X_D$ differs from control for continuous-type manufacturing. For example, the multivariate model used to control batch-type manufacturing processes include measurements of process parameters obtained throughout the manufacturing process as well as data about initial conditions (e.g., raw materials) and data about final conditions (e.g., quality and/or yield). This differs from continuous-type manufacturing processes because, for example, continuous-type manufacturing processes do not generally incorporate initial or final conditions because the process is "always-on."

For batch-type processes, the control actions (e.g., implementation of operating parameters) can include, for example, adjusting a recipe based on raw materials (e.g., initial conditions), a mid-process adjustment in response to a variation or change in operating conditions, an update of setpoint values at periodic intervals in the process, or combinations of these. Additionally, for batch-type processing, the multivariate statistics (e.g., $Y_{pred}$, DModX, $T^2$, and score t) are estimated based on estimated input values for $X_{MV}$ (e.g., future values of manipulated variables) and $X_D$ (future values of dependent variables) while the values of $X_K$ (past and present values of manipulated and dependent variables) are known. For batch-type processes, the multivariate model may include a plurality of localized batch models representing a portion of the batch-type process before and/or after control actions are implemented (e.g., by updating operating parameters of the system or process).

Figure 7:
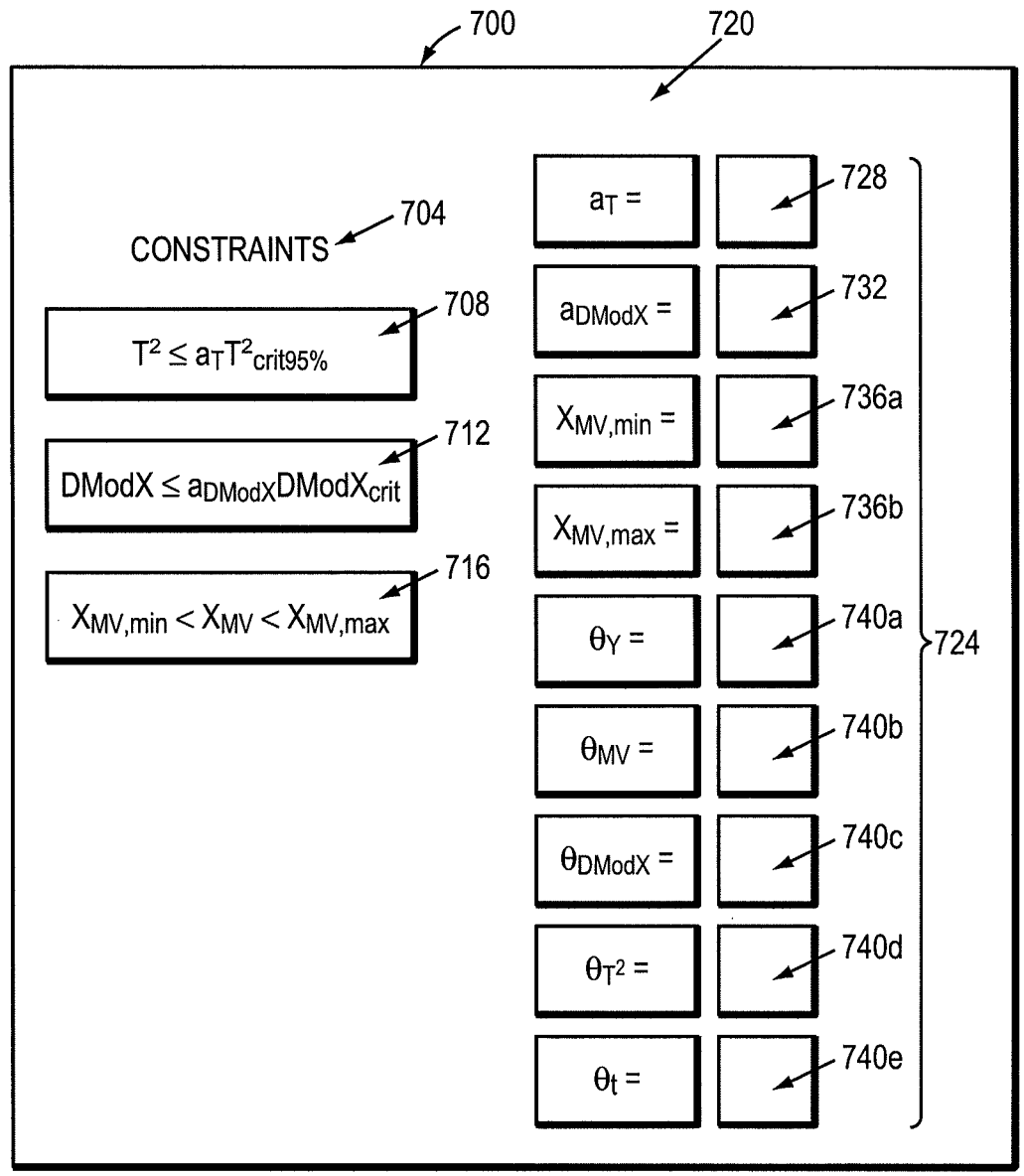
FIG. 7 is an exemplary user interface for specifying constraints to be applied to optimize a controller objective.

FIG. 7 is an exemplary user interface 700 for specifying constraints to be applied to optimize a controller objective. The user interface 700 includes an area 704 identifying constraints on an objective function (not shown) to be optimized. In some embodiments, the objective function is the objective function J discussed above with respect to FIG. 6. The area 704 illustrates a $T^2$ constraint 708, a DModX constraint 712, and an $X_{MV}$ constraint 716. Other constraints (not shown) can also be used depending on user preference. The user interface 700 includes a second area 720 identifying a plurality of fields 724 for displaying values associated with the constraints 708, 712, 716, or with a plurality of penalties of the objective function. Each of the values of the plurality of fields 724 can be a default value or a value specified by a user (e.g., via the user interface 700).

For example, the second area 720 includes an $a_T$ field 728 displaying the value of $a_T$ associated with the $T^2$ constraint 708. The $T^2$ constraint 708 relates measured or calculated values of $T^2$ against a user-specified threshold or critical value (e.g., 95% confidence) of $T^2$. The second area 720 includes an $a_{DModX}$ field 732 displaying the value of $a_{DModX}$ associated with the DModX constraint 712. The DModX constraint 712 relates measured or calculated values of DModX against a user-specified threshold or critical value (e.g., $DModX_{crit}$) of DModX. The second area also includes an $X_{MV,min}$ field 736a and an $X_{MV,max}$ field 736b both associated with the $X_{MV}$ constraint 716. The $X_{MV}$ constraint 716 constrains, e.g., the solver module, during a determination of $X_{MV}$ values to optimize a controller objective by provide minimum and maximum allowable values of $X_{MV}$ for the manufacturing process. These constraints allow the determined $X_{MV}$ values to converge on, for example, $T^2$ or DModX or within an acceptable design space.

The second area 720 also includes fields 740a-740e associated with penalties used in the objective function that is optimized. Specifically, the second area 720 includes a $\theta_Y$ field 740a that displays a penalty weight associated with Y variables in the objective function. The second area 720 includes a $\theta_{MV}$ field 740b that displays a penalty weight associated with the $E_{MV}$ relationship in the objective function J. The second area 720 includes a $\theta_{DModX}$ field 740c that displays a penalty weight associated with the $E_{DModX}$ relationship of the objective function J. The second area 720 includes a $\theta_{T2}$ field 740d that displays a penalty weight associated with the $E_{T2}$ relationship in the objective function J. The second area 720 includes a $\theta_t$ field 740e that displays a penalty weight associated with the $E_t$ relationship in the objective function J when the $E_t$ relationship is used.

Other constraints can also be used though not shown on the user interface 700. For example, a user or the system can specify minimum or maximum values of changes in $X_{MV}$ (e.g., $\Delta X_{MV}$). In some embodiments, the user can specify a penalty based on the size of $\Delta X_{MV}$. The user can specify minimum or maximum values of $Y_{pred}$ and/or specify a penalty based on the size of error in the Y variables (e.g., $Y_{err}$). Other representations of penalties or constraints associated with the multivariate statistics DModX and/or $T^2$ will also be apparent to those of skill (e.g., associating a penalty value with the size of the DModX value or associating a penalty with the size of the $T^2$ value beyond a maximum or threshold).

The above-described techniques can be implemented in digital electronic circuitry, or in computer hardware, firmware, software, or in combinations of them. The implementation can be as a computer program product, e.g., a computer program tangibly embodied in an information carrier, e.g., in a machine-readable storage device, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the technology by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The terms "module" and "function," as used herein, mean, but are not limited to, a software or hardware component which performs certain tasks. A module may advantageously be configured to reside on addressable storage medium and configured to execute on one or more processors. A module may be fully or partially implemented with a general purpose integrated circuit ("IC"), FPGA, or ASIC. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules. Additionally, the components and modules may advantageously be implemented on many different platforms, including computers, computer servers, data communications infrastructure equipment such as application-enabled switches or routers, or telecommunications infrastructure equipment, such as public or private telephone switches or private branch exchanges ("PBX"). In any of these cases, implementation may be achieved either by writing applications that are native to the chosen platform, or by interfacing the platform to one or more external application engines.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communications, e.g., a communications network. Examples of communications networks, also referred to as communications channels, include a local area network ("LAN") and a wide area network ("WAN"), e.g., the Internet, and include both wired and wireless networks. In some examples, communications networks can feature virtual networks or sub-networks such as a virtual local area network ("VLAN"). Unless clearly indicated otherwise, communications networks can also include all or a portion of the PSTN, for example, a portion owned by a specific carrier.

The computing system can include clients and servers. A client and server are generally remote from each other and typically interact through a communications network. The relationship of client and server arises by virtue of computer programs running on the respective computers and having a client-server relationship to each other.

Various embodiments are depicted as in communication or connected by one or more communication paths. A communication path is not limited to a particular medium of transferring data. Information can be transmitted over a communication path using electrical, optical, acoustical, physical, thermal signals, or any combination thereof. A communication path can include multiple communication channels, for example, multiplexed channels of the same or varying capacities for data flow.

Multiple user inputs can be used to configure parameters of the depicted user interface features. Examples of such inputs include buttons, radio buttons, icons, check boxes, combo boxes, menus, text boxes, tooltips, toggle switches, buttons, scroll bars, toolbars, status bars, windows, or other suitable icons or widgets associated with user interfaces for allowing a user to communicate with and/or provide data to any of the modules or systems described herein.

While the invention has been particularly shown and described with reference to specific embodiments, it should be understood by those skilled in the art that various changes in form and detail may be made therein without departing from the spirit and scope of the invention as defined by the appended claims.

The invention claimed is:

1. A computer-implemented method for controlling a batch-type manufacturing process with a finite duration, the method comprising:

receiving dependent variable data and manipulated variable data associated with the batch-type manufacturing process, the dependent variable data including measured past and present values of a first set of process parameters observed by one or more sensors, the manipulated variable data including measured past and present values of a second set of process parameters measured from a plurality of process tools, wherein the first set of process parameters, representative of dependent variables, and the second set of process parameters, representative of manipulated variables, are X-type variables in the batch-type manufacturing process;

determining, using a multivariate model of the manufacturing process, one or more multivariate statistics based on at least the dependent variable data and the manipulated variable data, wherein each multivariate statistic, which comprises a Hotelling value, a residual standard deviation value, a principal component score or a partial least squares component score, measures a deviation of the batch-type manufacturing process from a multivariate space of normal process behavior;

determining future values of the manipulated variables by optimizing an objective function that comprises $J=\theta_Y(Y_{SP}-Y_{pred})^2+\theta_{MV}(E_{MV})^2+\theta_{DModX}(E_{DModX})^2+\theta_{T2}(E_{T2})^2+\theta_t(E_t)^2$, wherein (i) $Y_{SP}$ represents at least one setpoint or target value for Y-type yield variables representative of yield or quality at the end of the finite duration of the batch-type manufacturing process, (ii) $Y_{pred}$ represents at least one predicted value for the yield variables, (iii) $E_{MV}$ represents an amount of deviation in the manipulated variable data from a desired trajectory subject to a penalty weight $\theta_{MV}$, (iv) $E_{DModX}$ represents an amount of the residual standard deviation value subject to a penalty weight $\theta_{DModX}$, (v) $E_{T2}$ represents an amount of the Hotelling value subject to a penalty weight $\theta_{T2}$, (vi) $E_t$ represents an amount of the principal component score or the partial least squares component score subject to a penalty weight $\theta_t$, (vii) and $\theta_Y$ represents a penalty weight;

adjusting at least one of the second set of process parameters based on the future values of the manipulated variables.

2. The method of claim 1, wherein the second set of process parameters, represented by the manipulated variables, are controlled during the manufacturing process.

3. The method of claim 2, wherein the first set of process parameters, represented by the dependent variables, are not directly controlled during the manufacturing process.

4. The method of claim 1, further comprising modifying the present or future values of the manipulated variables based on the past or present values of the manipulated variables and of the dependent variables.

5. The method of claim 1, wherein determining future values of the manipulated variables further comprises satisfying a controller objective.

6. The method of claim 5, wherein satisfying a controller objective comprises optimizing the objective function by associating process data, values for the yield variables, result data, or any combination thereof of the manufacturing process.

7. The method of claim 6, wherein the objective function includes one or more constraints on the dependent variable data, the manipulated variable data, values for the yield variables, the multivariate statistic, or any combination thereof.

8. The method of claim 7, wherein the one or more constraints are user-specified.

9. The method of claim 7, wherein the one or more constraints are associated with penalties for deviating from the multivariate model.

10. The method of claim 5, wherein the controller objective is the objective function comprising a quadratic-type function and satisfying the controller objective further comprises minimizing a parameter of the objective function.

11. The method of claim 1, further comprising;
determining desired values for the yield variables or desired multivariate statistic associated with the end of the finite duration of the batch type manufacturing process; and
adjusting the second set of process parameters based on the future values of the manipulated variables to achieve at least one of the desired values for the yield variables or the desired multivariate statistic.

12. The method of claim 1, further comprising estimating future values of the dependent variables using a dependent variable model based on the future values of the manipulated variables, the past or present values of the dependent variables, or any combination thereof.

13. The method of claim 1, wherein optimizing the object function penalizes deviation of the multivariate statistic from the multivariate model.

14. The computer-implemented method of claim 1, further comprising:
estimating future values of the dependent variables based on the future values of the manipulated variables; and
providing at least one of the future values of the dependent variables or the future values of the manipulated variables as inputs to the multivariate model.

15. The computer-implemented method of claim 1, further comprising:
estimating the predicted value for the yield variables based on the future values of the manipulated variables; and
providing the predicted value for the yield variables as inputs to the objective function.

16. A multivariate controller for a batch-type manufacturing process with a finite duration, the controller comprising:
a hardware control module in communication with a plurality of process tools and a plurality of sensors to monitor manipulated variable data from the process tools and dependent variable data from the sensors, the control module including a multivariate model for determining one or more multivariate statistics based on at least the manipulated variable data and the dependent variable data, each multivariate statistic comprising a Hotelling value, a residual standard deviation value, a principal component score or a partial least squares component score, and each multivariate statistic measuring a deviation of the batch-type manufacturing process from a multivariate space of normal process behavior,
wherein the dependent variable data includes measured past and present values of a first set of process parameters observed by the plurality of sensors and the manipulated variable data includes measured past and present values of a second set of process parameters, wherein the first set of process parameters, representative of dependent variables, and the second set of process parameters, representative of manipulated variables, are X-type variables in the batch-type manufacturing process; and
a hardware solver module to: i) receive, from the multivariate model, the one or more multivariate statistics, and ii) optimize an objective function using the multivariate statistics determined from the multivariate model to generate future values of the manipulated variables for providing to the plurality of process tools, wherein the objective function comprises $J = \theta_Y (Y_{SP} - Y_{pred})^2 + \theta_{MV} (E_{MV})^2 + \theta_{DModX}(E_{DModX})^2 + \theta_{T2}(E_{T2})^2 + \theta_t(E_t)^2$, wherein (i) $Y_{SP}$ represents at least one setpoint or target value for Y-type yield variables representative of yield or quality at the end of the finite duration of the batch-type manufacturing process, (ii) $Y_{pred}$ represents at least one predicted value for the yield variables, (iii) $E_{MV}$ represents an amount of deviation in the manipulated variable data from a desired trajectory subject to a penalty weight $\theta_{MV}$, (iv) $E_{DModX}$ represents an amount of the residual standard deviation value subject to a penalty weight $\theta_{DModX}$, (v) $E_{T2}$ represents an amount of the Hotelling value subject to a penalty weight $\theta_{T2}$, (vi) $E_t$ represents an amount of the principal component score or the partial least squares component score subject to a penalty weight $\theta_t$, (vii) and $\theta_Y$ represents a penalty weight.

17. The controller of claim 16, wherein the controller adjusts one or more parameters of the plurality of process tools based on the future values of the manipulated variables.

18. The controller of claim 16, wherein the solver module is adapted to provide the future values of the manipulated variables to a score model to generate predicted values for the solver module of one or more statistical data.

19. The controller of claim 18, wherein the score model provides the predicted statistical data to the control module and the solver module.

20. The controller of claim 16, wherein the solver module is adapted to provide the future values of the manipulated variables to a dependent variable model to estimate future values of the dependent variables.

21. The controller of claim 20, wherein the dependent variable model provides the future values of the dependent variables to the multivariate model to improve future determination of the multivariate model.

22. The controller of claim 16, wherein the solver module generates the future values of the manipulated variables based on a controller objective.

23. The controller of claim 22, wherein the controller objective optimizes the objective function comprising a quadratic-type function associated with the manufacturing process.

24. The controller of claim 22, wherein the controller objective includes one or more constraints on the dependent variable data, the manipulated variable data, values for the yield variables, the multivariate statistic, or any combination thereof.

25. The controller of claim 24, wherein the one or more constraints are user-specified.

26. The controller of claim 24, wherein the one or more constraints are associated with penalties for deviating from the multivariate model.

27. The controller of claim 16, wherein the solver module is a constrained optimization solver.

28. The controller of claim 16, wherein the control module comprises the solver module.

29. A system for controlling a batch-type manufacturing process with a finite duration, the system comprising:
a hardware data acquisition means for acquiring manipulated variable data associated with the manufacturing process, including measured past and present values of a set of process parameters measured from a plurality of process tools; and acquiring dependent variable data associated with the manufacturing process, including measured past and present values of a second set of process parameters observed by a plurality of sensors, wherein the first set of process parameters, representative of dependent variables, and the second set of process parameters, representative of manipulated variables, are X-type variables in the batch-type manufacturing process;
a hardware multivariate control means incorporating a multivariate statistical model for receiving at least the manipulated variable and dependent variable data and determining multivariate statistical information that measures a deviation of the batch-type manufacturing process from a multivariate space of normal process behavior, wherein the multivariate statistical information comprises one or more of a Hotelling value, a residual standard deviation value, a principal component score or a partial least squares component score;

a hardware process control means for determining future values of the manipulated variables by optimizing an objection function using at least the multivariate statistical information determined by the multivariate control means, the objective function comprising $J=\theta_Y(Y_{SP}-Y_{pred})^2+\theta_{MV}(E_{MV})^2+\theta_{DModX}(E_{DModX})^2+\theta_{T2}(E_{T2})^2+\theta_t(E_t)$, wherein (i) $Y_{SP}$ represents at least one setpoint or target value for Y-type yield variables representative of yield or quality for the end of the finite duration of the batch-type manufacturing process, (ii) $Y_{pred}$ represents at least one predicted value for the yield variables, (iii) $E_{MV}$ represents an amount of deviation in the manipulated variable data from a desired trajectory subject to a penalty weight $\theta_{MV}$, (iv) $E_{DModX}$ represents an amount of the residual standard deviation value subject to a penalty weight $\theta_{DModX}$, (v) $E_{T2}$ represents an amount of the Hotelling value subject to a penalty weight $\theta_{T2}$, (vi) $E_t$ represents an amount of the principal component score or the partial least squares component score subject to a penalty weight $\theta_t$, (vii) and $\theta_Y$ represents a penalty weight, wherein the process control means is configured to adjust at least one of the second set of process parameters representative of manipulated variables based on the future values of the manipulated variables.

30. The system of claim 29, wherein the future values of the manipulated variables determined by the process control means optimize or satisfy a control objective.

* * * * *